US 12,030,056 B2

(12) United States Patent
Patel

(10) Patent No.: US 12,030,056 B2
(45) Date of Patent: Jul. 9, 2024

(54) KIT, APPARATUS AND METHOD FOR A PORTABLE NUCLEIC ACID ASSAY

(71) Applicant: Hasu Diagnostics, Marlow (GB)

(72) Inventor: Alpesh Patel, Marlow (GB)

(73) Assignee: Hasu Biotech Ltd (GB)

( * ) Notice: Subject to any disclaimer, the term of this patent is extended or adjusted under 35 U.S.C. 154(b) by 12 days.

(21) Appl. No.: 17/520,705

(22) Filed: Nov. 7, 2021

(65) Prior Publication Data

US 2022/0143598 A1    May 12, 2022

(30) Foreign Application Priority Data

Nov. 7, 2020 (GB) .................................... 2017611

(51) Int. Cl.
*C12Q 1/6844* (2018.01)
*B01L 3/00* (2006.01)
*B01L 7/04* (2010.01)

(52) U.S. Cl.
CPC ........... *B01L 3/5029* (2013.01); *B01L 3/5457* (2013.01); *B01L 7/04* (2013.01); *C12Q 1/6844* (2013.01); *B01L 2200/023* (2013.01); *B01L 2200/10* (2013.01); *B01L 2200/16* (2013.01); *B01L 2200/18* (2013.01); *B01L 2300/021* (2013.01); *B01L 2300/042* (2013.01); *B01L 2300/047* (2013.01); *B01L 2300/0609* (2013.01); *B01L 2300/069* (2013.01); *B01L 2300/1805* (2013.01)

(58) Field of Classification Search
CPC .. C12Q 2527/101; C12Q 1/6844; C12Q 1/68; B01L 3/5029; B01L 2300/042; B01L 2300/047; B01L 2200/16
See application file for complete search history.

(56) References Cited

U.S. PATENT DOCUMENTS

2012/0115212 A1    5/2012  Weigl

FOREIGN PATENT DOCUMENTS

WO      2017100765 A1      6/2017
WO      WO-2020146826 A1 *  7/2020  ......... A61B 10/0051

OTHER PUBLICATIONS

Weigl et al., "Non-instrumented Nucleic-Acid Amplification Assay," SPIE, vol. 6886, p. 688604-1 to 688604-12 (Year: 2008).*
GB Search report for GB2115977.7.

* cited by examiner

*Primary Examiner* — Young J Kim

(57) ABSTRACT

The self-contained kit comprises methods for receiving and preparing the biological samples for the nucleic acid amplification and sensing the presence of the target assay. The kit consists of a self-heating pack to provide the heat for nucleic acid sample preparation and amplification processes. The change of the amplification is indicated through colorimetric or turbidity sensing and detected through a mobile phone camera and associated mobile application for photographic scanning of physical or chemical differences of the samples to produce the test results.

10 Claims, 6 Drawing Sheets

KIT, APPARATUS AND METHOD FOR A PORTABLE NUCLEIC ACID ASSAY

RELATED APPLICATIONS

This patent application claims priority from prior-filed United Kingdom Application GB 2017611.1 filed 7 Nov. 2020, incorporated herein by reference.

FIELD OF THE INVENTION

The present invention is a kit for the biological sample receiving, processing and sensing of nucleic acid amplification.

BACKGROUND

Nucleic acid based infection diagnostic testing requires controlled laboratory facilities or arrangement, other precautionary measurements to collect the samples and trained people to run the test in a controlled environment or send the test samples to test centers or laboratories where the test can be conducted. Thus, tremendous efforts and resources are required from the beginning of swab collection, transporting the samples and subsequently for testing the samples. The process of sample collection is it-self challenging and risk of catching infections to the swab handler, besides to collect samples and sending to testing sites and carrying out molecular tests takes time and the whole logistic process and protocol is established to ensure the sample identity, generating test results and coordinating with relevant clinicians and ultimately reached out to the patients.

Besides the sample collection and logistic challenges, the current nucleic acid-based testing methods are manual or in some large facilities adapt massive large-scale lab automation processes. Moreover, human intervention is inevitable for front-end sample collection and sample preparation process, the same is for back-end detection process of nucleic acid amplification which is also slow due to the amplification and detection simultaneous operation happening within the machine and it occupies the space, so scalability is challenging for large scale testing within the time and a major roadblock for releasing the information to the patients.

Sequencing technologies can be used for scaleup testing with the use of barcoded sample templates in parallel for 10s of thousand samples at a time. However, this does not solve the problem of the front-end sample preparation process steps to prepare ten thousand samples for sequencing processes. Also, the sequencing-based technologies not only require manual processes to prepare sequencing templates but analysis of the entire pool of sequencing data of samples as well requires professional expertise and manual execution, thus there is an additional burden of computing system and time to analyse the data followed by the meaningful reports interpretation for each of the sample. Thus, existing technology and processes does not solve the problems of needs for automated testing at rapid, low cost and outside of the laboratory environment.

All these challenges could be resolved if the testing can be performed directly by the users, similar to blood sugar and pregnancy test kits performed directly by the users.

The art may be further described by the following patents and papers:

U.S. Pat. No. 9,469,871B2—Methods and apparatus for point-of-care nucleic acid amplification and detection. U.S. Pat. No. 7,943,348B2—Method and apparatus for amplifying nucleic acids U.S. 61/435,250 Systems and methods for sample use maximization. U.S. Ser. No. 10/283,217B2 Systems and methods for detecting infectious diseases. U.S. 62/269,904 Methods, compositions, kits and devices for rapid analysis of biological markers. PNAS Sep. 15, 2020 117 (37) 22727-22735—Rapid isothermal amplification and portable detection system for SARS-CoV-2.

SUMMARY OF THE INVENTION

In one aspect there is provided a kit for the sensing of biological samples comprising: a sampling swab; heat activation reagents; nucleic acid assay reagents; a first nucleic acid assay chamber containing the nucleic acid assay reagents; a second nucleic acid assay chamber containing control reaction reagents; a heating reaction chamber having an open end for receiving the first reaction chamber and the heat activation reagents; and an insulated housing for receiving the heating reaction chamber.

The kit may comprise a printed barcode identifying the type of nucleic acid assay.

The kit may comprise a printed instructions and test chart for interpretation, preferably which test chart comprises printed indications of positive and negative results.

The kit may comprise a narrowing slot for squeezing out saliva from the sampling swab.

The kit may comprise a printed QR code encoding a unique kit code for a given kit and a link to a mobile app or website.

The first nucleic acid assay chamber may comprise a closing cap and the nucleic acid assay reagents may be located inside the closing cap and arranged to be released into the first nucleic acid assay chamber when the closing cap is turned to a closed position.

The kit may comprise a liquid cell lysis buffer for mixing with the sampling swab.

The second nucleic acid assay chamber may be chemically isolated from but physically connected to the first nucleic acid assay chamber.

The kit may comprises a timer.

According to a second aspect there is provided a method of detecting a biological sample using a portable nucleic acid device having a sampling swab, a nucleic acid reaction chamber, a heat activator, heating reaction chamber, insulated housing. The method comprise the steps of: providing a saliva sample using the sampling swab; starting a nucleic acid reaction by mixing a nucleic acid reaction mixture with the saliva sample in the nucleic acid reaction chamber; starting an exothermic reaction using the heat activator in the heating reaction chamber; placing the nucleic acid reaction chamber in the heating reaction chamber; and comparing a result of the nucleic acid reaction to a control.

The result may be a color or turbidity.

The method may comprise users information, testing date, results outcome and geographical location.

The method may comprise a printed barcode identifying the type of nucleic acid assay.

The method may comprise further comprising a printed instructions and color test chart for interpretation.

The method may comprise, wherein the printed instructions further comprise printed indications of positive and negative results.

The method may comprise squeezing out saliva from the sampling swab through a narrowing slot of the nucleic acid reaction chamber The method may comprise comprising placing the heating reaction chamber in the insulated housing.

The method may comprise using a mobile device to capture a printed QR code on the kit to follow a link to a mobile app or website.

The method may comprise turning a closing cap on the nucleic acid reaction chamber to close the cap and release the nucleic acid reaction mixture into the nucleic acid assay chamber.

The method may comprise mixing a liquid cell lysis buffer with the sampling swab.

The method may comprise starting a control reaction in a control chamber and placing that control chamber into the heating reaction chamber at substantially the same time as the nucleic acid reaction chamber then timing both reactions.

BRIEF DESCRIPTION OF THE DRAWINGS

Various objects, features and advantages of the invention will be apparent from the following description of embodiments of the invention, as illustrated in the accompanying drawings. The drawings are not necessarily to scale, emphasis instead being placed upon illustrating the principles of various embodiments of the invention.

DETAILED DESCRIPTION

Figure 1:
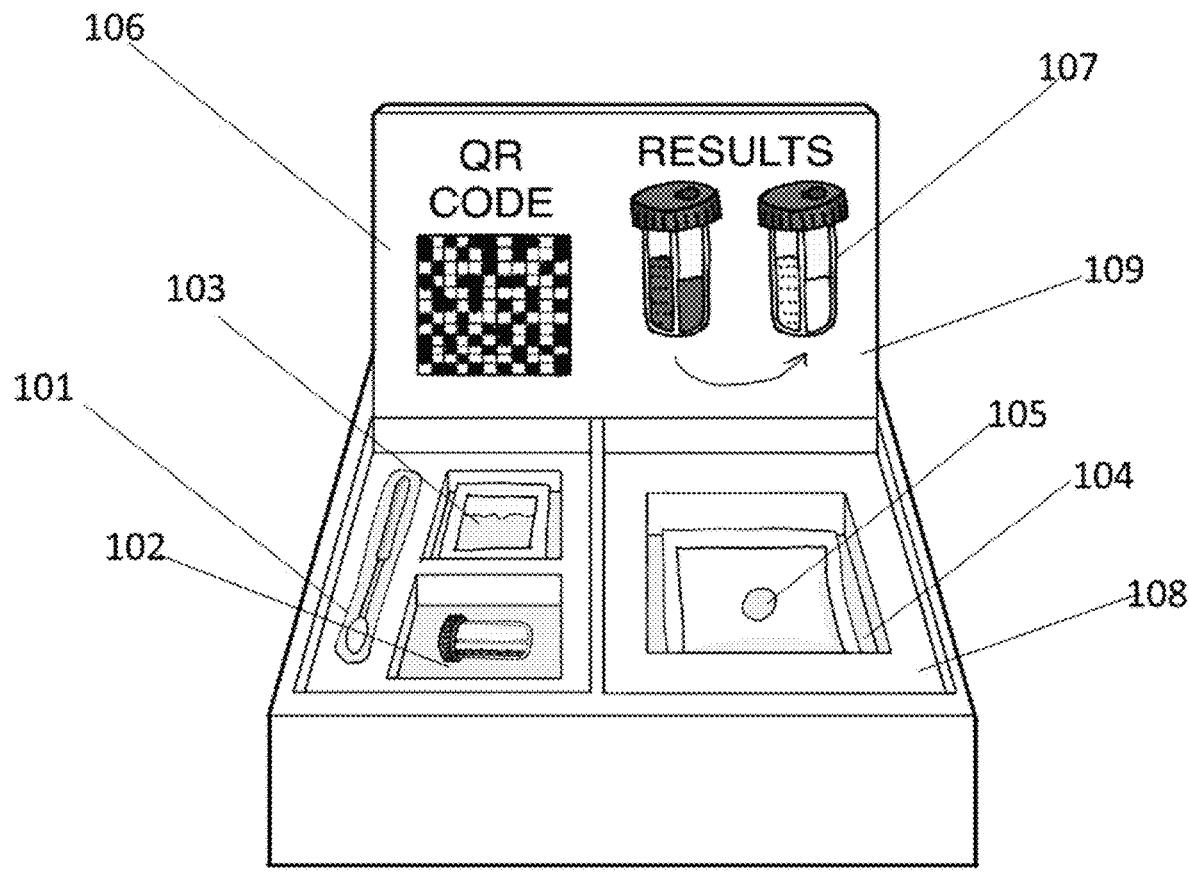
FIG. 1 is a perspective view of a self-contained diagnostic test kit.
Figure 2:
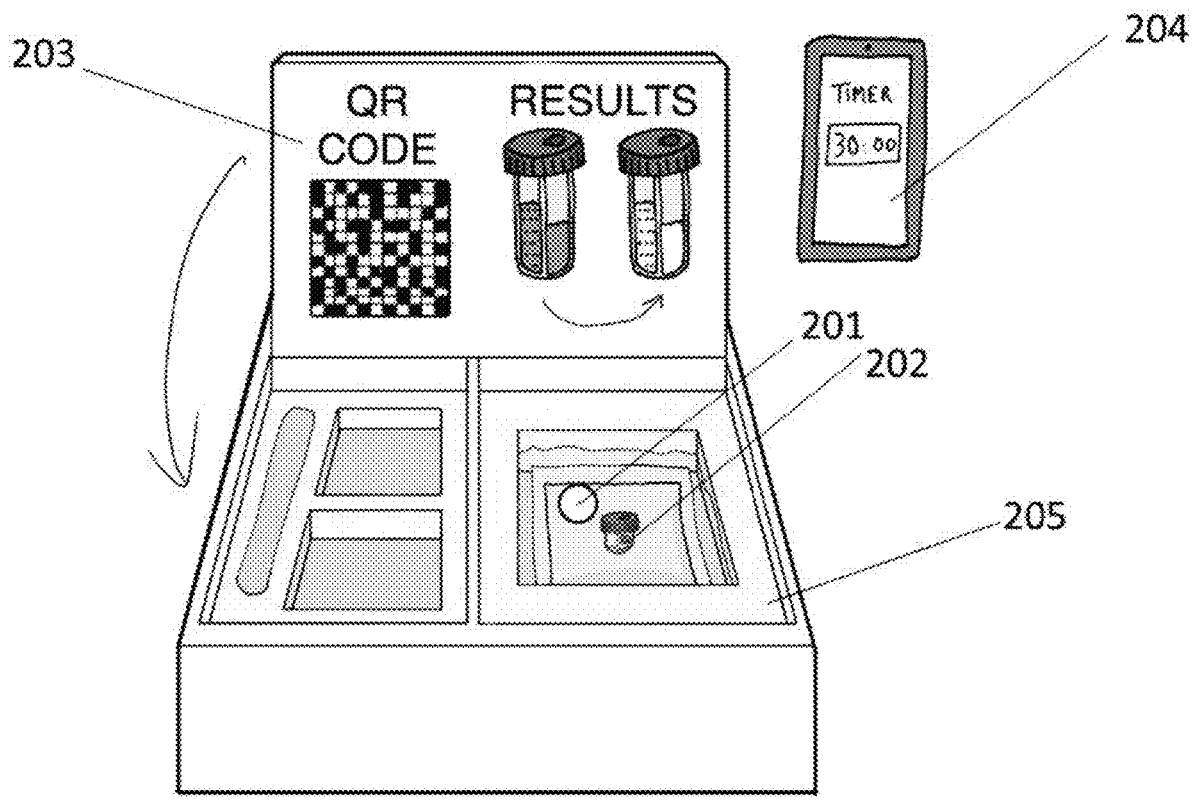
FIG. 2 is a perspective view of a test kit preparation for nucleic acid amplification.
Figure 3:
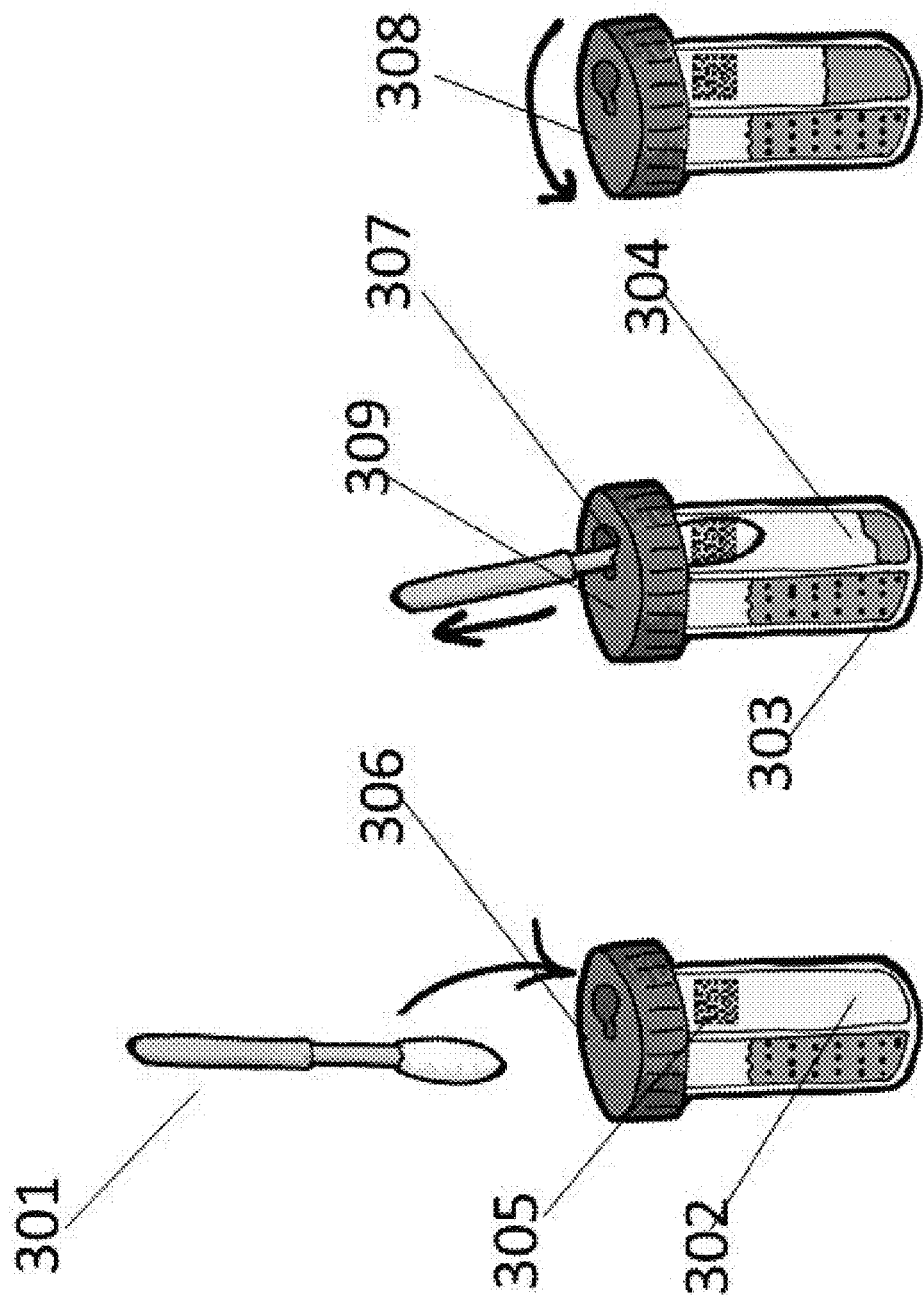
FIG. 3 is a side view of a saliva sample being introduced to a test kit.
Figure 4:
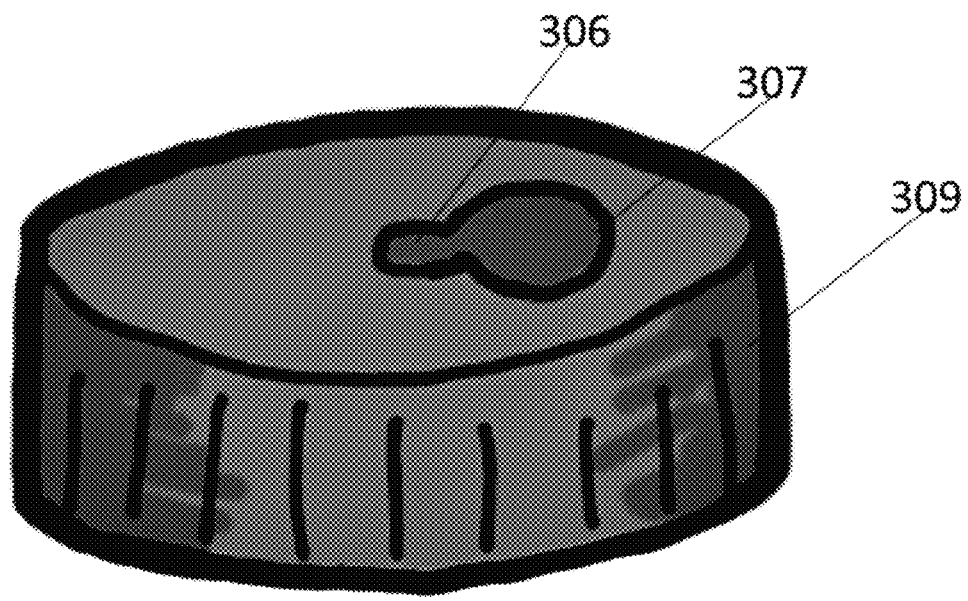
FIG. 4 is a perspective view of a sample introduction slot.
Figure 5:
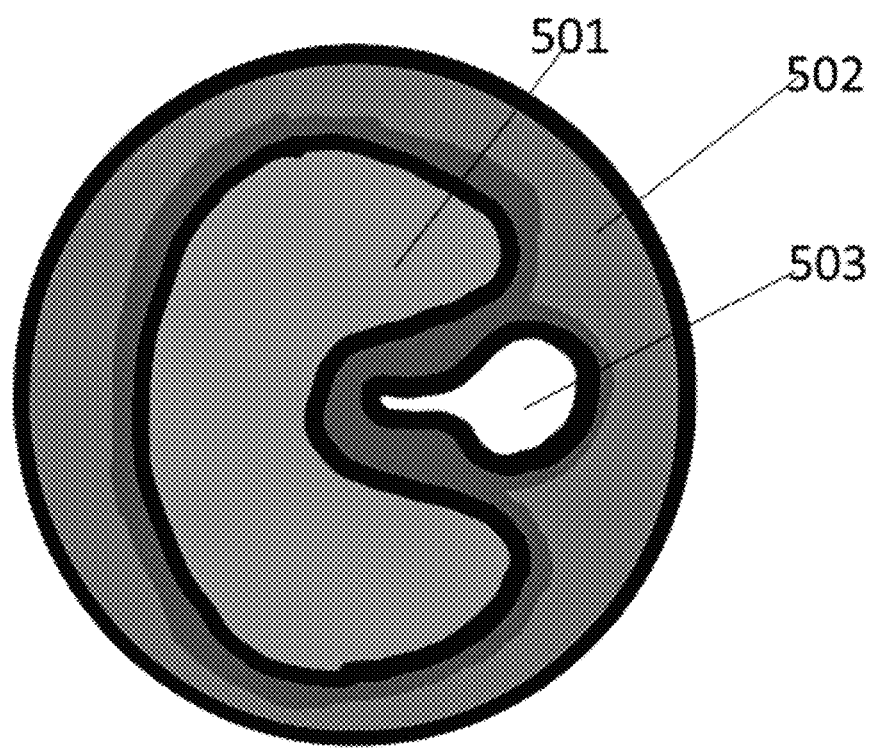
FIG. 5 is top view of a reagent storage section.
Figure 6:
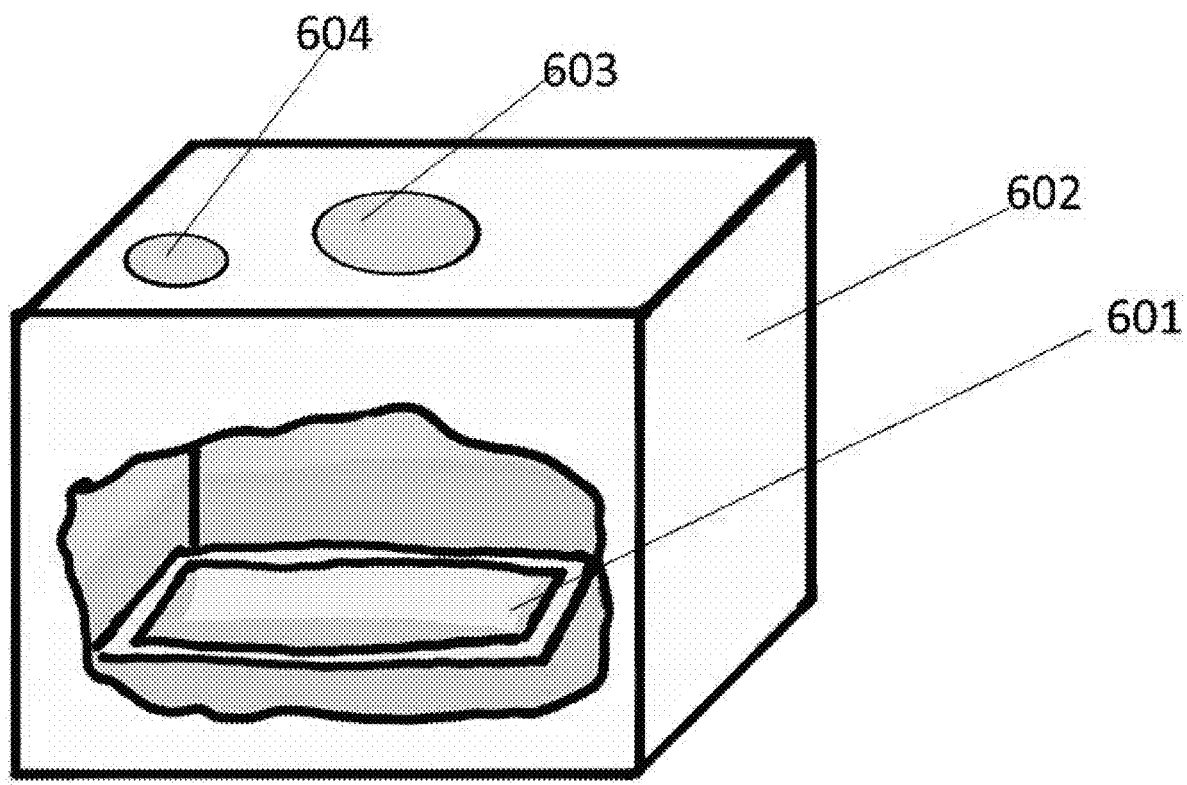
FIG. 6 is a perspective view of a reaction box.
Figure 7:
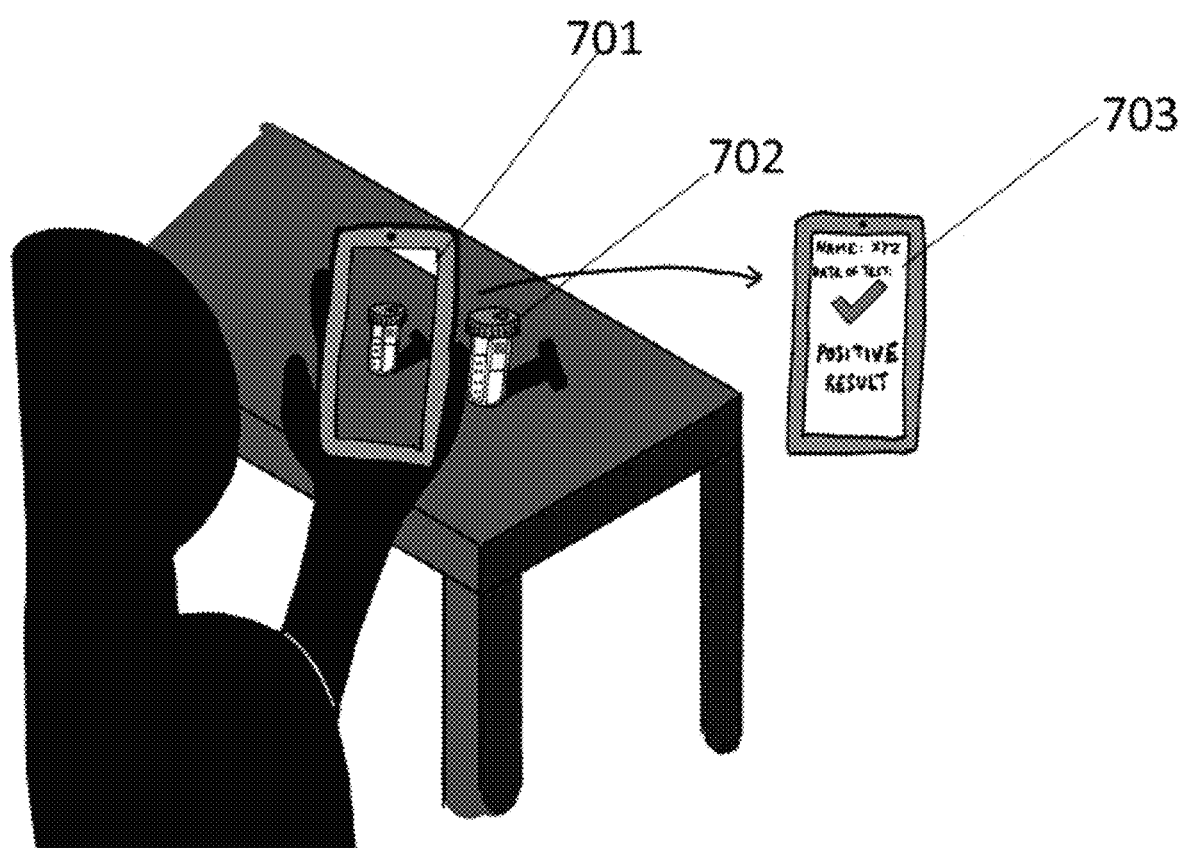
FIG. 7 is an illustration of a test result interpretation.

The present kit and method describes a self-contained, easy to use sample to result kit for receiving a biological sample and mixing the reagents for sample preparation which includes resuspension or dissolving the sample and lysis, the desired pathogen cells or any target source, in a rapid process and preparing the sample for the nucleic acid amplification.

The kit operates manually without any skilled or trained human intervention, once the sample is loaded and placed into the kit, a simple twist of the kit cap, the reagents get released and the heat activation process initiates the heat production. The test is portable and can be run by any layman at home environment, offices, care homes, clinics and any other remote locations. The users will use the mobile application for taking a photo of the finished reaction test kit to see the colour or turbidity for ability to use the automated test result generation on the app and store the information for future use.

The mobile app data can also be used for the database buildup monitoring and control of infectious disease such as covid-19 or winter flu outbreaks. The databases can be used for triage analysis of test results, given the users' information and the geographical location along with personal mobility over the last 7 days. That information combines to link the disease carrier and trail the origin of the infection. The mobile app generated data can be used to develop a roadmap of infection hotspots and enable the healthcare stakeholders in decision making.

Self-Contained Test Kit

The self-contained test kit 1 is a housing having accessories and reagents to perform the direct to consumer (D2C) molecular diagnosis of the infectious diseases e.g. COVID-19 or any other respiratory virus diseases.

The housing contains 101 Swab slot for the swabs, 102 Reaction pot slot for the reaction pot with all reagents, 103 Heat activator slot contains the activation medium to add to the heat pack, 104 Heat pack comprises a reaction chamber with heat generating material described earlier and contains a reaction area slot for placing the reaction pot to carry out the test and, 105 Heat pack contains the reaction pot slot, 106 Printed QR code for the mobile app, 107 Printed test results interpretation instruction, 108 the insulation mold box and 109 Insulated box lid.

Sample Reaction Pot:

The reaction pot 302 is made of two compartments, the first compartment is for the control reaction 303 for test verification and the other compartment is the test compartment 304, the test compartment has a narrowed entry 306 over the cap 309 for the sample deposition, the user will insert the swab through the wider part of the key hole and pull it out via the narrow section 307 thus this will squeeze the swab and the sample will be deposited into the reaction section 304 of the pot. The user will then twist the cap 308 to the closed position of the reaction pot, to release the reagent 501 into both the control and sample side reaction chamber or section. Subsequently, the user will place the reaction pot in the reaction area 202 and add the heat activator 103 through the activator addition slot 201 to initiate the heating and hence the reaction.

Heating Pack Box:

The self-contained test kit provides the heat required for the nucleic acid amplification through the chemical or crystallization exothermic heat pack box 602. The heat activation initiator or activator 103 when mixed with the heat pack 601, the heat production reached to the nucleic acid amplification temperature preferably for the isothermal amplification temperature range from the 50 degree Celsius to 75° C.

The heat product can be controlled through the choice of heat-activator, heat pack material and the kit thermal insulation box 205 R value. The thermal insulation of the insulation box is made through the foam moulding of the size of the heat pack box, the foam preferable the closed cell polyurethane foam with the R value 6 to 10 $m^2K/W$.

The heat pack 601 of the reaction chamber 602 test box kit is made up of anhydrous alkali oxide e.g. calcium oxide (Quicklime) and a mix of quicklime and charcoal or magnesium oxide and calcium oxide mixture from 10% to 100% calcium oxide and 25% to 0% charcoal, the charcoal can be activated anhydrous charcoal, preferably the mixture is 75% CaO (Calcium Oxide) and 25% activated anhydrous charcoal. The heat activator 103 added to the Heat test box 602 via the hole 604 for heat activation for the nucleic acid amplification. The heat activator is water or acidic water with hydrochloric or sulfuric acid or added sodium bisulphite 0.1M to 0.5M), preferably the 0.1M acidic water with HCl (hydrochloric acid and 1% glycerin or water) and glycerol (50:50 mix) and once added, the heat pack produces the heat up to 110° C. to 70° C. The desire temperature between 60° to 70° C. for over 30 to 60 minutes can be achieved through providing the appropriate mixture of the calcium oxide and charcoal and water with acids and glycerol, the preferable mixture ratio of the calcium oxide: charcoal and 1% Glycerol of 0.1M hydrochloric acid is 3:0 and 9:40 respectively.

Nucleic Acid Amplification and Sensing

The kit contains the reagents 304 for the biological sample, preferably respiratory viruses, extraction from the swab 301 and the cell lysis buffer in liquid form, which comes in contact with the sample swab once the sampling process is completed. The liquid cell lysis buffer may be stored in a receptacle of the cap with a pierceable film. Thus when the swab enters the narrowed slot it pierces the film to mix saliva sample and lysis buffer. The preferable lysis buffer consist of 1% SDS solution with 10 mM EDTA.2Na solution, the other lysis buffer also effective with Triton X100 and Proteinase K enzyme to ensure the RNAse is effectively inactivated by the Proteinase K enzyme. The nucleic acid amplification reagents 501 are stored in the reaction pot cap 502. The turning of the cap 308 releases the reagents for the nucleic acid amplification. The reagents are mixed in both reaction 304. All the amplification reagents mix get homogenize through simple finger flicking on the chambers and followed by shaking process to take the amplification mix into the reaction section of the pot.

The kit contains separate control chamber 303 for the nucleic acid control reaction, which is connected to the test chamber in order for both reactions to proceed under the same conditions and time to validate reactions and compare results. The control contains pre-stored templated reagent mix.

The isothermal nucleic acid amplification reagents contain reagents for the target nucleic acid amplification. The amplification reagent consists of pH, buffering, stabilizing agents, polymerase, primers, probes, nucleotides. The recipe can be 1 mM Tris-HCl, 50 mM KCl, and 1.5 mM MgCl2, pH 8.3, and 50-100 micromolar pH Indicator dye, preferably phenol red. The reaction mix also consists of reverse transcriptase enzyme M-MLV 100 and 200 units and Bst polymerase 4 to 8 units per reaction and 50 micromolar concentration primers sets of 20 to 40 base long for specific target nucleic acid amplification. The reagents contain pH indicator dye Phenol red from pH 8.5 pink to pH 7.5 yellow colour change. The nucleic acid amplification is detected through the change of the colour of the reaction after amplification of the reaction as referenced in the literature (Viet Loan Dao Thi et al, A colorimetric RT-LAMP assay and LAMP-sequencing for detecting SARS-CoV-2 RNA in clinical samples, Science Translational Medicine 12 Aug. 2020: Vol. 12, Issue 556).

The control reaction compartment contains the same recipe of the target reaction compartment, The recipe can be 1 mM Tris-HCl, 50 mM KCl, and 1.5 mM MgCl2, pH 8.3, and 50-100 micromolar pH Indicator dye, preferably phenol red. The reaction mix also consists of reverse transcriptase enzyme M-MLV 100 and 200 units and Bst polymerase 4 to 8 units per reaction and 50 micromolar concentration primers sets of to 40 base long for specific target nucleic acid amplification but it consists of the known specific target template together in the range of 1 micro micromolar or less or between 1000 to 10000 copies of the template, the preferred known template is human Ribonuclease P (RNaseP) gene fragment, so when the reaction pot get heated to reaction temperature (60-65° C.) the control reaction which contains the know templates get amplify in the same condition as a reference reaction.

Test Results

The method for the test result interpretation consists of the Mobile application, which users download through the barcode scan prior to running the test. The Mobile app assists the users for adding the personal information such as name, age, gender, address, country of residence etc, the Mobile application assists users further when the test starts, the Mobile app has the built in timer to monitor the timing of the test. The Mobile application method asks users to press the timer tab of the mobile to start the monitoring the test time and when the desired time of the test is achieved the Mobile app alerts the users through the sounds and vibration indication. The Mobile app timer 4 alerts the users to finish the test, the user takes the reaction pot 702 from the reaction chamber box and scans the QR code of the reaction pot to match the pre-reaction barcode, once the QR code matches, mobile camera take the picture shots 701 for both control and target reaction sections. If the control shows positive reaction and the target reaction chamber shows no reaction then the results have shown a negative test outcome. If the control and the target reaction chamber show positive change then it is a positive test outcome 703. If the controls do not show the positive change and the target reaction chamber shows the positive change then the test outcome is not valid.

In case, users do not prefer to use a mobile app for the result interpretation, the test kit box contains the results interpretation chart printed 107 on the box to directly see the changes of the test outcomes.

The invention claimed is:

1. A kit for the sensing of biological samples comprising:
   a sampling swab;
   heat activation reagents;
   nucleic acid assay reagents;
   a first nucleic acid assay chamber containing the nucleic acid assay reagents, including target amplification primers;
   a second nucleic acid assay chamber containing control reaction reagents;
   a common closing cap for both nucleic acid assay chambers, which closing cap comprises an amplification buffer arranged to be released into the first nucleic acid assay chamber when the closing cap is turned to a closed position;
   a heating reaction chamber having an open end for receiving both the first and second nucleic acid assay chambers simultaneously and the heat activation reagents;
   an insulated housing for receiving the heating reaction chamber; and
   a narrowing slot in the closing cap for squeezing out saliva from the sampling, swab.

2. A kit according to claim 1, further comprising printed instructions and a test chart for interpretation, which test chart comprises printed indications of positive and negative results.

3. A kit according to claim 1, further comprising a liquid cell lysis buffer for mixing with the sampling swab.

4. A kit according to claim 1, wherein the second nucleic acid assay chamber is chemically isolated by a dividing wall from the first nucleic acid assay chamber.

5. A kit according to claim 1, further comprises a timer.

6. A kit according to claim 1, wherein the heat activation reagents comprise an acidic buffer.

7. A kit according to claim 6, wherein the acidic buffer comprises hydrochloric acid and glycerol.

8. A kit according to claim 1, wherein the heat activation reagents comprise 0.1 M to 0.5 M hydrochloric or sulfuric acid.

9. A kit according to claim 1, wherein the heat activation reagents comprise sodium bisulphite aqueous solution.

10. A kit according to claim 1, wherein the open end of the heating reaction chamber has separate openings for receiving the heat activation reagents separate from the first and second nucleic acid assay chambers.

* * * * *